(12) United States Patent
Chung et al.

(10) Patent No.: US 11,674,134 B2
(45) Date of Patent: Jun. 13, 2023

(54) METHOD OF ISOLATING NUCLEIC ACIDS AND THE SYSTEM THEREOF

(71) Applicant: IMAGEN BIOSCIENCE CO., LTD, Taichung (TW)

(72) Inventors: Ting-Hao Chung, Taichung (TW); Min-I Lin, Taichung (TW)

(73) Assignee: IMAGEN BIOSCIENCE CO., LTD, Taichung (TW)

( * ) Notice: Subject to any disclaimer, the term of this patent is extended or adjusted under 35 U.S.C. 154(b) by 221 days.

(21) Appl. No.: 17/143,545

(22) Filed: Jan. 7, 2021

(65) Prior Publication Data

US 2021/0214717 A1    Jul. 15, 2021

(30) Foreign Application Priority Data

Jan. 9, 2020    (TW) ................. 109100773

(51) Int. Cl.
*C12N 15/10*    (2006.01)
(52) U.S. Cl.
CPC .................. *C12N 15/1013* (2013.01)
(58) Field of Classification Search
None
See application file for complete search history.

(56) References Cited

U.S. PATENT DOCUMENTS 7,078,224 B1    7/2006  Bitner et al.
8,703,931 B2    4/2014  Euting et al.

FOREIGN PATENT DOCUMENTS

CN    108841920 A    11/2018

*Primary Examiner* — Patrick T Lewis
(74) *Attorney, Agent, or Firm* — Muncy, Geissler, Olds & Lowe, P.C.

(57) ABSTRACT

The invention discloses a method of isolating nucleic acid and the system thereof, which relates to the following process: (1) providing a biological sample containing cells; (2) performing a cell concentration procedure; (3) performing a magnetic separation procedure through a magnetic separation unit; (4) performing a suspension procedure through a suspending unit; (5) performing a lysis procedure through a lysis unit; and (6) performing a nucleic acid extraction procedure to extract the nucleic acids from the biological samples; wherein the cell concentration procedure does not involve any means of centrifugation. Therefore, the method is simple and efficient, and it is particularly favorable in full automation of nucleic acid isolation. Furthermore, the method and the system as a whole further include a clarification procedure executed by a clarification unit without using centrifugation means, so that improves the quality of nucleic acid isolation.

5 Claims, 9 Drawing Sheets

METHOD OF ISOLATING NUCLEIC ACIDS AND THE SYSTEM THEREOF

CROSS-REFERENCE TO RELATED APPLICATIONS

This application claims the benefit of Taiwan Application No. 109100773 filed on Jan. 9, 2020, the content of which are hereby incorporated by reference in their entirety.

FIELD OF THE INVENTION

The invention relates to a method and a system for isolation of nucleic acids and, more particularly, to a method and a system for magnetic separation of nucleic acids.

BACKGROUND OF THE INVENTION

It is well known that nucleic acids in organisms contain a wealth of genetic information and have nowadays become an essential material for biomedical research, drug development and clinical applications. With the development of research approaches and analytical methods, people pay particular attention to efficiency and quality of nucleic acid isolation in various applications. Therefore, how to isolate nucleic acids from diverse types of biological samples more efficiently, to obtain good quality and good recovery rate of nucleic acids for subsequent applications, has become an important goal in this field.

In view of the above objectives, people began to develop automated nucleic acid separation technology and equipment, in which magnetic separation approach is widely used automated nucleic acid separation method. The basic principle of magnetic separation method is to use magnetic solid-phase carriers to absorb nucleic acids from biological samples, and with devices that can control magnetic carriers (e.g., magnetic disks or rods), to move or transfer magnetic carriers between various tubes and reagents to separate solid-phase matter and liquid phase matter, thereby replacing manual pipe operation for the purpose of separating or extracting nucleic acids. Because the magnetic separation method is very suitable for mechanical automation control, in addition to high efficiency, stable operation quality, low contamination risk and other favorable effects, it is more conducive to apply standard process to the nucleic acid separation procedures, establish consistency, and further develop high-throughput automated nucleic acid separation technology and equipment.

However, even though magnetic separation technology advances the automation of nucleic acid separation, as for the existing magnetic separation art, there are still limitations on the pre-treatment of biological samples. Specifically, due to that nucleic acids are present in a wide variety of biological samples, such as blood, cultured cells, feces, fresh tissue, fixed tissue, formalin-fixed and paraffin-embedded (FFPE) tissue, bacterial culture, bio-fermentation fluids, etc., and in biological samples from diverse sources, various biological materials (e.g., blood, tissue, cells, bacterial culture/fermentation fluid precipitation, etc.) often produce debris, impurities and precipitation after lysis, some semi-solid or viscous substances may be formed to significantly interfere with the magnetic separation of pipe operations, and result in unnecessary sample depletion and reduced recovery rate of nucleic acid separation. On the other hand, if there are too many impurities in the lysate/solution, it will significantly affect the solution environment of subsequent nucleic acid separation, and consequently deteriorate the quality and performance of nucleic acid isolation.

In general, in response to the above technical defects, most of the existing technologies use centrifugal or filtration methods to remove debris, impurities and precipitation, thus not eliminating the disadvantages derived from manual operation, and rely on centrifugal means. Another solution is to perform the lysate clarification step after lysing the biological sample. In this way, the disadvantageous effects of impurities may be eliminated by replacing the solution environment of the nucleic acid. However, it is still difficult to avoid the restrictions of dependence on centrifugal methods/means, making it difficult to achieve the goal of "fully automated nucleic acid separation".

In view of the above-mentioned disadvantages that hinder the automated separation of nucleic acids, U.S. Pat. No. 7,078,224B1 proposes a technical solution that uses magnetic particles made of silica gel or pH-dependent ion exchange materials to perform chemical modifications (e.g., glycidyl-alanine modified magnetic beads and glycidyl-histidine modified silica beads); and specific solutions and procedures are required therein to separate nucleic acids. Despite this method may eliminate the use of centrifugal means, a specific type of magnetic beads made of modified material is required. At the same time, to exert the expected technical effect, specific reagent conditions are also required to match with this specific type of magnetic beads for creating suitable solution environment. Therefore, the operating conditions are relatively strict, so that the practical use is substantially limited.

Another example is the formalin-fixed and paraffin-embedded (FFPE) tissue samples, which are important source of nucleic acids for molecular diagnosis and therapeutic decision. The pre-processing for such biological samples are complicated. The deparaffinization must be done prior to isolating nucleic acids. Moreover, since the cells or tissues in the biological sample are fixed, the biomolecules (e.g., proteins and nucleic acids) of the biological samples are crosslinked. In this case, the unfavorable effects from debris or insoluble impurities in the lysate of biological sample are apparently worsened.

U.S. Pat. No. 8,703,931B2 proposes a method for separating nucleic acids from FFPE biological samples, which also discloses a magnetic separation method. According to the method, to avoid clogging the tip of the pipette, the cell debris and other impurities from the lysate were removed effectively through magnetic particles. A specifically configured container made of hydrophobic plastic material is used for carrying the lysate containing paraffin, and the melting properties of paraffin are also used therein. The paraffin in the container is heated by temperature control device to melt (above 50° C.) first, and then cooled, so that paraffin cures again, forms a ring-shaped precipitation at the edge of the container. At this point, the liquid sample can be automatically and accurately drew out by the machine. In this way, it effectively avoids the paraffin and debris clogging the piper tips, and leaves paraffin precipitation in the container to complete this separation procedure. In practice, this method is based on the special design utilizing paraffin precipitation. In order to get rid of the debris/impurities in lysate, it also requires the setting of magnetic rings and magnetic devices correspondingly to control the movement and spatial distribution of beads. The process does not need to use a specific solution of chaotropic salt and may be exempted from centrifugal steps. However, since the method utilizes coordinating properties of container made of specific material and the paraffin under delicate temperature control to reach the magnetic separation results, the separation target is limited to the paraffin itself. As for removal of other insoluble impurities, the method is still limited. Furthermore, regarding the implementation of this method, a specially configured container, corresponding operation settings and temperature controllers are also required to exert their technical effects, therefore, this method is still difficult to popularize piratically.

Recently, China Patent Application No. CN108841920 proposes a method for automated separation of nucleic acids from FFPE biological samples. The proposed invention utilizes magnetic separation method to extract nucleic acids, it uses magnetic beads and magnetic control devices to spatially control the cell/tissue according to the predefined transfer plan, to avoid debris suspension interfering the operation of the pipetting. However, despite the method does not depend on centrifugal means, organic solvents (e.g., xylene) are required at the deparaffinization stage, hence it is difficult to avoid the drawbacks (e.g., pollution and toxicity) of conventional nucleic acid extraction method using organic solvents.

In view of the above, it can be learned that, for the automated technology of isolating nucleic acids from any kinds of biological samples, the pre-treatment process can dominate the performance and quality of automated operation. Therefore, based on the above-mentioned technical needs and limitations, the present invention provides a simple, efficient and universal nucleic acid isolation method and its system for all kinds of biological samples, which can achieve excellent isolation performance without using any centrifugal methods or special equipment in the pre-treatment process.

SUMMARY OF THE INVENTION

One of the objectives of the present invention is to provide a method for isolating nucleic acids and the corresponding operation system that can replace centrifugal method or step for realizing the fully automated nucleic acid isolation.

According to the above-mentioned objectives, the present invention provides a method for isolating nucleic acids, which includes the following steps: (1) providing a biological sample containing a plurality of cells; (2) performing a cell concentration procedure on the biological sample, wherein a cell grabbing reagent and a magnetic carrier are mixed with the biological sample, and then the magnetic carrier forms a magnetic mass along with the plurality of cells; (3) performing a first magnetic separation procedure to separate the magnetic mass; (4) performing a suspension procedure, adding a suspension reagent to the magnetic mass, mixing evenly, and enabling the plurality of cells to be resuspended in the suspension reagent, so as to form a first solution; (5) performing a lysis procedure, adding a lysis reagent into the first solution to lyse the plurality of cells in the first solution, so as to form a second solution; and (6) performing a nucleic acid extraction procedure to extract nucleic acids from the second solution; wherein the cell concentration procedure does not involve any means of centrifugation.

According to the aforesaid objectives, the present invention further discloses a method for isolating nucleic acids, wherein the step (5) further comprises a clarification procedure after the plurality of cells are lysed; wherein a clarification reagent is added to the first solution having the lysed cells and the lysis reagent, and mixed evenly to form the second solution.

According to the aforesaid objectives, the present invention further discloses a method for isolating nucleic acids, wherein the clarification reagent is monovalent ion solution free of alcohols, ketones, or chaotropic salt reagents.

According to the aforesaid objectives, the present invention further discloses a method for isolating nucleic acids, wherein the cell grabbing reagent is aqueous solution containing 10% to 70% by volume of low-molecular-weight alcohols, acetone or a mixture thereof.

According to the aforesaid objectives, the present invention further discloses a method for isolating nucleic acids, wherein the magnetic carrier contains silica, nitrocellulose, or polyvinyl alcohol.

According to the above-mentioned objectives, the present invention provides a system for isolating nucleic acids, which includes the following units: a cell concentration unit used for performing a cell concentration procedure, wherein a cell grabbing reagent and a magnetic carrier are mixed with a biological sample containing a plurality of cells, and then the magnetic carrier forms a magnetic mass along with the plurality of cells; a magnetic separation unit used for performing a first magnetic separation procedure to separate the magnetic mass; a suspension unit used for adding a suspension reagent to the magnetic mass, mixing evenly, and enabling the plurality of cells to be resuspended in the suspension reagent, so as to form a first solution; a lysis unit used for performing a lysis procedure, adding a lysis reagent into the first solution to lyse the plurality of cells in the first solution, so as to form a second solution; and a nucleic acid extraction unit used for performing a nucleic acid extraction procedure to extract nucleic acids from the second solution; wherein the cell concentration procedure dose not involve any means of centrifugation.

According to the aforesaid objectives, the present invention further discloses a system for isolating nucleic acids, further including a clarification unit used for performing a clarification procedure after the plurality of cells are lysed; wherein the clarification unit provides a clarification reagent and the clarification reagent is added to the first solution having the lysed cells and the lysis reagent, and then mixed evenly to form the second solution.

According to the aforesaid objectives, the present invention further discloses a system for isolating nucleic acids, wherein the cell grabbing reagent is aqueous solution containing 10% to 70% by volume of low-molecular-weight alcohols, acetone, or a mixture thereof.

According to the aforesaid objectives, the present invention further discloses a system for isolating nucleic acids, wherein the magnetic carrier contains silica, nitrocellulose, or polyvinyl alcohol.

According to the aforesaid objectives, the present invention further discloses a system for isolating nucleic acids, wherein the clarification reagent is monovalent ion solution free of alcohols, ketones, or chaotropic salt reagents.

Based on the nucleic acid isolation method and system previously disclosed in the present invention, the present invention provides a simple and easy-to-obtain cell capture reagent and clarification reagent, which can be used in combination with any solvent system as well as the currently available commercial manual or automated products commonly used according to the user's needs. It is especially suitable for application in fully automated nucleic acid isolation to eliminate the use of centrifugal means. Thus, the disclosed method and its system according to the present invention greatly improves the quality and performance of nucleic acid isolation.

DETAILED DESCRIPTION

To allow those who skilled in the art to further understand the purposes, technical features and advantages of the present invention, and to enable them to implement the invention, the following detailed description when taken in conjunction with the accompanying drawings are provide herein to specify the technical features and embodiments of the present invention. Preferred examples are also provided herein for further explanation of the present invention. The accompanying drawings, which are incorporated into the specification, illustrate specific embodiments of the invention and, together with the detailed description of the specific embodiments, serve to explain the principles of the invention. It is not and does not need to be drawn in its entirety according to the actual situation. And the technical detail of the implementation known to those skilled in this field is no longer stated.

In view of the demand for automated isolation of nucleic acids, the present invention provides a nucleic acid isolation method and system, which use simple reagents and steps to promote magnetic carrier to grab cells in biological samples. Consequently, the cells are effectively concentrated, and the impurities are simultaneously eliminated. Therefore, the method and system can be widely used in various types of nucleic acid isolation procedures. Furthermore, besides concentrating the cells, the method and system provided in the present invention are suitable for processing the lysed biological samples to generate clarified lysate, which is favorable for nucleic acid isolation. Relevant implementation of the present invention and the resultant effects and advantages will be explained along with the examples in the following description.

First, the nucleic acid stated in the present invention means DNA, RNA and DNA/RNA complex, including but not limited to: plasmid DNA, artificial amplification DNA (i.e., amplified DNA), genomic DNA, chromosomal DNA, RNA fragments, total RNA, mRNA, and so forth. However, in view of the frequency and demand of practical application, DNA isolation is a preferred embodiment of the present invention.

Figure 1:
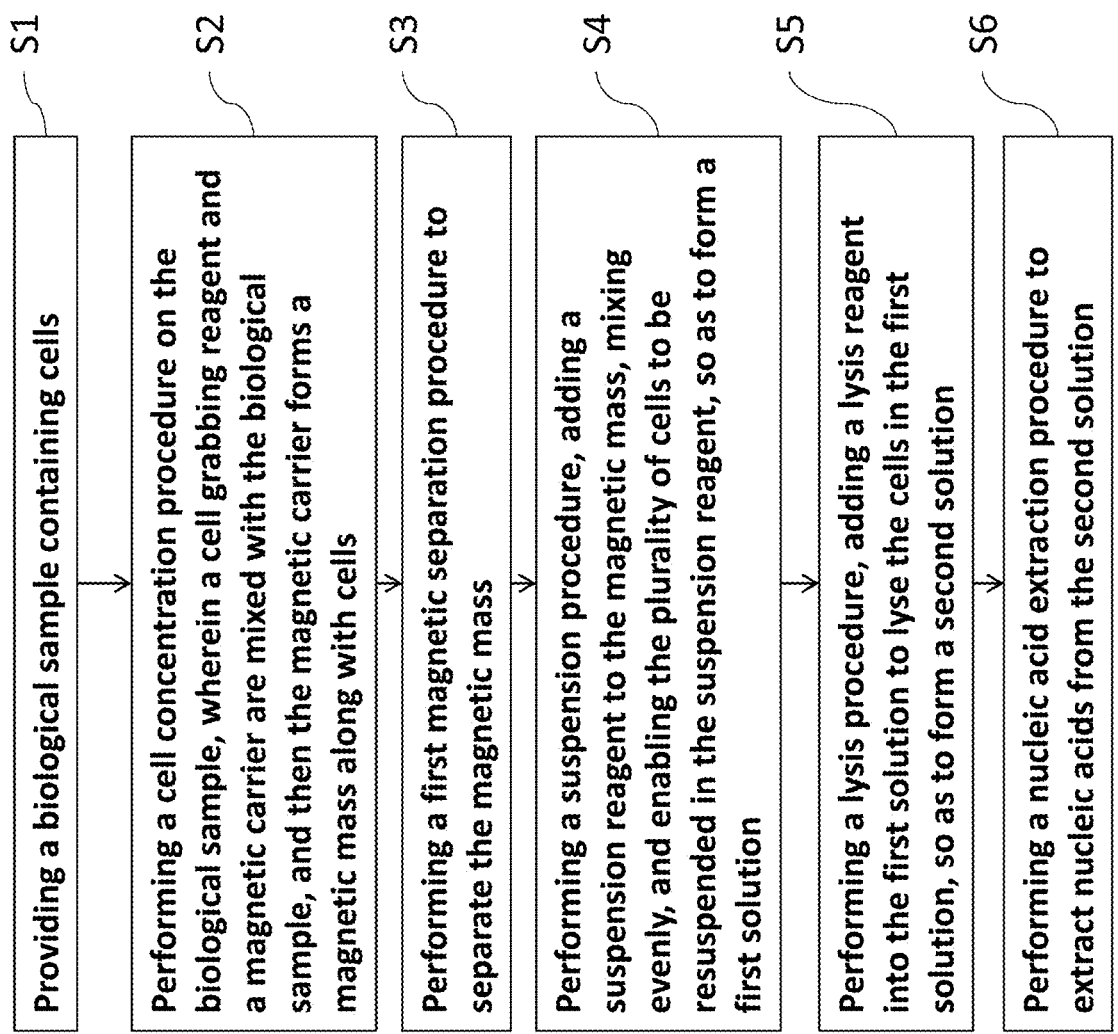
FIG. 1 shows a flowchart of the nucleic acid separation method according to an embodiment of the present invention.

According to the preferred embodiment of the present invention and the nucleic acid separation flowchart shown in FIG. 1, the steps of the nucleic acid isolation method of the present invention are as follows:

Step S1 is firstly providing biological samples, which refers to a variety of biological materials containing nucleic acids. Specific examples include but are not limited to: clinical samples (e.g., blood, primary culture cells, fresh tissue, frozen tissue, semen, feces), cultured bacteria, in vitro cultured cells, tissue culture and its cultured medium, microbial fermentation fluid, etc., wherein the biological samples all contain cells as a source of nucleic acid. It needs to be emphasized that the term of "cells" used herein covers all kinds of biological samples and experimental samples applicable to the present invention, and is not limited to living cells, which means, as long as the conditions are appropriate, fixed or embedded tissues is also applicable to the method of the present invention.

After obtaining a specific biological sample, step S2, the cell concentration procedure, is carried out. The cell concentration procedure utilizes the cell grabbing reagent provided according to the present invention with unlimited types of magnetic carrier. The magnetic carrier can "grab" the cells by non-chemical bonding (e.g., physical adsorption caused by Van der Waals force). Since "grabbing cells" means the magnetic carries temporarily adsorbs, retains, carries the cells in the micro-environment by the intermolecular attraction force, the procedure involving grabbing dose not altering the status or nature of the cells, as well as the nucleic acids in those cells. Based on these characteristics, according to the preferred embodiment of the present invention, the cell concentration procedure is to add cell grabbing reagent and magnetic carriers to the biological samples, and gently mixed evenly, so that magnetic carriers can grab cells from various biological samples, to achieve the effect of concentrating cells. By means of the interaction between the cells and magnetic carriers, the cells and magnetic carriers form the magnetic mass. However, it should be understood that, due to the diversity of particle size of different magnetic carrier and the various size of different cell types, the capacity of magnetic carriers to capture cells (calculated as total cell volume per unit of magnetic carrier) are consequently diversified, but the overall performance on grabbing cells is not substantially affected. Therefore, the magnetic mass generally refers to the solid-phase substances or colloidal substances formed by dispersion, suspension or aggregation in the solution after the magnetic carrier grabs the cells. The form, appearance or volume of the magnetic mass is not limited herein.

To achieve the technical effects of the cell concentration procedure, according to the preferred embodiment of the present invention, the cell grabbing reagent is preferably the aqueous solution containing low-molecular-weight alcohols, acetone, or mixture of different low-molecular-weight alcohol or acetone aqueous solution. In the following description, all the descriptive concentrations of cell grabbing reagent are defined as the final concentration. In other words, the concentration of the cell grabbing reagent should be the concentration of the cell grabbing reagent in the working solution after the target solution is added with cell grabbing reagent to form this working solution. This is a general scientific definition/principle for describing the solute concentration in a solution, and it can be easily understood by skilled persons in the field. Thus, based on this principle, the volume percentage concentration (final concentration) of the cell grabbing reagent according to the present invention ranges preferably from 10% to 70%, and more preferably ranges from 20% to 60%. The low-molecular-weight alcohol is preferably the methanol, ethanol, and isopropanol. These preferred options are commonly used reagents in this technical field, which is convenient for the present invention. Additionally, according to a preferred embodiment of the present invention, the cell grabbing reagent may not contain any salt and is independent of any buffer system, therefore, there is no ion concentration related concerns on the integrity of the cells to be concentrated. These facts certainly elaborate the simplicity and the practicality of this method.

Then, step S3 is performed, mainly includes a first magnetic separation procedure, with the purpose of separating the magnetic mass formed by the cell concentration procedure for subsequent nucleic acid separation isolation steps. As previously mentioned, since those skilled in the art are usually aware of the principle of magnetic separation, the process will not be detailed herein. Specifically, the magnetic carrier is an important tool of magnetic separation technology, which has the characteristics of sensing magnetic force and moving with the magnetic force, and this tool is widely used in nucleic acid isolation. The magnetic carrier described in the present invention refers generally to a magnetic solid-phase carrier such as particles, magnetic beads, or thin films. According to one preferred embodiments of the present invention, the magnetic carrier is preferably in the form of particles or beads, therefore, the magnetic carrier will be generically called as "magnetic beads" hereinafter, but it does not limit that the magnetic separation system of the present invention using magnetic beads as magnetic carriers. In addition, according to the universal usage of the present invention, the aforementioned magnetic carrier is preferably the commonly used magnetic beads, and more preferably is the commercial product or easy-to-obtain product. More specifically, the magnetic carrier of the present invention is preferably made of materials containing silica, nitrocellulose or polyvinyl alcohol, which also includes composite materials consisting of different compositions, or modified magnetic beads to adapt for specific purpose.

In view of above, because the existing magnetic separation technology for biological sample is limited by numerous pre-treatment requirements, thus, even in the existing automated system, biological samples usually need to be carefully pretreated to comply with a specified criteria before adding magnetic beads to isolate nucleic acids (e.g., magnetic beads have to be added only after cell homogenization is properly done for subsequent separation). Therefore, it is still difficult to achieve the goal of "fully automated isolation of nucleic acid". In contrast, the method provided in the present invention can be used in the cell concentration procedure. Specifically, the magnetic beads are added to the biological samples along with the cell grabbing reagent to the biological sample, so that the magnetic beads act as the magnetic carrier for carrying the cells with the help of cell grabbing reagent, and the fully automated device can take over the subsequent magnetic separation steps. Therefore, according to the nucleic acid isolation method provided in the present invention, not only the cell concentration procedure does not require any centrifugal steps, in the convergence of the next procedure, there is no need for any centrifugal steps, and it can followed by the first magnetic separation procedure, thus eliminating manual operation, to achieve the goal of full automation.

In the first magnetic separation procedure, magnetic devices that can generate magnetic forces are used to control the magnetic beads carrying the cells, so that the magnetic device takes the beads together with the cells entirely out of the original solution without damaging the cells. In this way, as long as sufficient magnetic beads are used, and the operating conditions of the magnetic device are appropriate, the cells in the biological sample can be fully concentrated, and the magnetic mass is used as the material for subsequent isolation of nucleic acids, thus eliminating interference of non-cellular substances, solutions, and debris. According to the characteristics of the present invention is suitable for various type of automated nucleic acid separation device, the magnetic device is not the only option, while the existing commercially available devices are the preferred options.

Furthermore, the types of magnetic beads used in different procedures of the present invention are not limited. According to one preferred embodiment of the present invention, the magnetic beads used in the cell concentration procedure are the same as all magnetic separation procedures, which is more conducive to the separation efficiency. However, for the purpose of improving the performance of the cell concentration procedure or enhancing the specific effect of subsequent procedures to isolate nucleic acids, the present invention also does not exclude the use of different types (including different materials, structures, compositions, constituents, particle size or physical properties) of magnetic beads at different steps, to elaborate the advantages of the present invention.

After separating the magnetic mass, the suspension procedure of the step S4 is performed. In this step, a suspension reagent is added to the separated magnetic mass and mixed gently and evenly to enable the cells grabbed on the magnetic mass to be resuspended in the suspension reagent, so that the resuspended cells and suspension reagent form a first solution. According to the concept of the present invention, in this suspension procedure, the conditions of the first solution can be further adjusted in accordance with the type of biological sample and the characteristics of the target cells, such as adding buffer or cell-specific additives, in order to maintain the integrity and stability of the cells. These measures are conducive to maintaining the quality of subsequent nucleic acid isolation.

Furthermore, when the cell resuspension described herein occurs, the interaction status between the cells and the magnetic beads is not limited, and the cell resuspension works without any prior step of enabling the cells to desorb from the magnetic beads. In other words, in the suspension procedure, the desorption of the cells from the magnetic beads can be promoted by using appropriate vortex. Therefore, the cells can be resuspended in the suspension reagent in their original form. However, according to specific embodiment, the use can apply this suspension procedure flexibly according to their demands, designs and nucleic acid isolation workflow. Even if the cells are still carried by the magnetic beads, the cells can resuspended in the solution by dispersing the magnetic mass. This mode of operation is also they fall within the scope of "resuspension" referred in the present invention. Nevertheless, according to one preferred embodiment of the present invention, the cells are desorbed from the magnetic beads prior to the subsequent steps.

Step S5 mainly involves a lysis procedure in which the lysis reagent is added to the first solution with the aim of lysing the cells contained in the first solution. The lysis reagent are used to disintegrate tissue structures and cellular structures (e.g., cell membranes, cell walls, intracellular organelles) so that the cells break up and release the nucleic acids contained therein, thus forming a second solution containing the lysed product and its solution. It is readily for skilled persons to understand that this second solution can be considered as a lysate or homogenate. Those skilled in the field can also easily understand that different biological samples, depending on tissue or cellular characteristics, have corresponding lysis reagents, which do not exclude the addition of specific chaotropic agents or enzymes. Alternatively, the use can apply external forces (e.g., vortex) or raise the reaction temperature with the use of the lysis reagent to enhance lysis or homogenization effect. Therefore, the reagents and reaction conditions used in this step are not limited. In fact, the variety of currently commercial or customary lysate reagents can be used. As long as the biological samples containing the nucleic acids to be isolated can be lysed well and homogenated, any reagent and reaction condition is applicable to the present invention.

According to another embodiment of the present invention, in step S6, a clarification procedure (lysate clearance) may be further included for the purpose of clarifying the lysate product and making the whole solution more suitable for subsequent nucleic acid isolation steps. The clarification procedure should be performed after the lysis reagent is added to the first solution to cleave the cell. At this time, the first solution contains the lysed cells and the lysis reagent, so the clarification procedure is practically performed at this time to add the clarification reagent to the first solution containing the lysed cells and the lysate reagent and mixed evenly to form a second solution (e.g., the clarified lysate or homogenate) for subsequent nucleic acid extraction.

Conventionally, centrifugal or filtration methods are often used to remove suspended debris and impurities from lysate or homogenate, which is also detrimental to automation. Besides, in general, the commonly used clarification procedures nowadays often need to use reagents containing reagent containing chaotropic salts (chaotropic reagents, which include by not limited to sodium iodide, sodium perchlorate, guanidine thiocyanate, guanidine isothiocyanate or guanidine hydrochloride) to treat the solution to be clarified for enhancing the clarification effect. However, the effectiveness of the chaotropic salt depends on its ratio in the working environment, thus increasing the complexity of the reagent composition for clarification. However, according to the clarification procedure provided by the present invention, it uses a simple composition of clarification reagent, when the clarification reagent is added to the lysate or homogenate and evenly mixed, this clarification procedure can achieve the expected clarification effect. And processed solution obtained from the clarification procedure can be used directly to cooperate with the magnetic beads for magnetic separation work, and completely replace centrifugal or filtration methods. Hence this procedure can be directly applied in existing automated processes, systems and equipment. In addition, regarding the clarification reagents used in current technical field, if the reagents used in various procedures contain alcohols and even ketone solvents, the nucleic acids will consequently retain on the magnetic beads due to the incomplete desorption, and thus the recovery rate of nucleic acids can be affected, and affect the recovery rate of nucleic acids. This disadvantage has a particularly negative effect on the extraction effectiveness of trace nucleic acids. Therefore, according to one of the preferred embodiments of the present invention, the clarification reagent is a monovalent ion solution free of alcohols, ketones, or chaotropic salt reagents. The monovalent ion solution includes but is not limited to ammonium acetate ($NH_4OAc$), sodium acetate (NaOAc), potassium acetate (KOAc), ammonium chloride ($NH_4Cl$), and potassium chloride (KCl).

After obtaining a second solution containing the lysed product, the following step S6, the nucleic acid extraction procedure, is performed. This nucleic acid extraction procedure generally refers to all procedures or extracting target nucleic acids (e.g., various DNA and RNA) from lysate or homogenate, and therefore, whether it is manual operation to extract nucleic acids or mechanically automated extraction of nucleic acids, they fall within the scope of nucleic acid extraction procedures referred to in the present invention. According to one preferred embodiment of the present invention, the nucleic acid extraction procedure is preferably an automated magnetic extraction procedure to obtain a high quality and abundant nucleic acids in an efficient, consistent and reliable automated process. In the nucleic acid extraction procedure, with regard to the principle of nucleic acid extraction, including but not limited to: magnetic bead adsorption, washing, neutralization, elution and other processes, it can be readily understood for those skilled in the field, therefore, it will not be detailed again herein.

Figure 2:
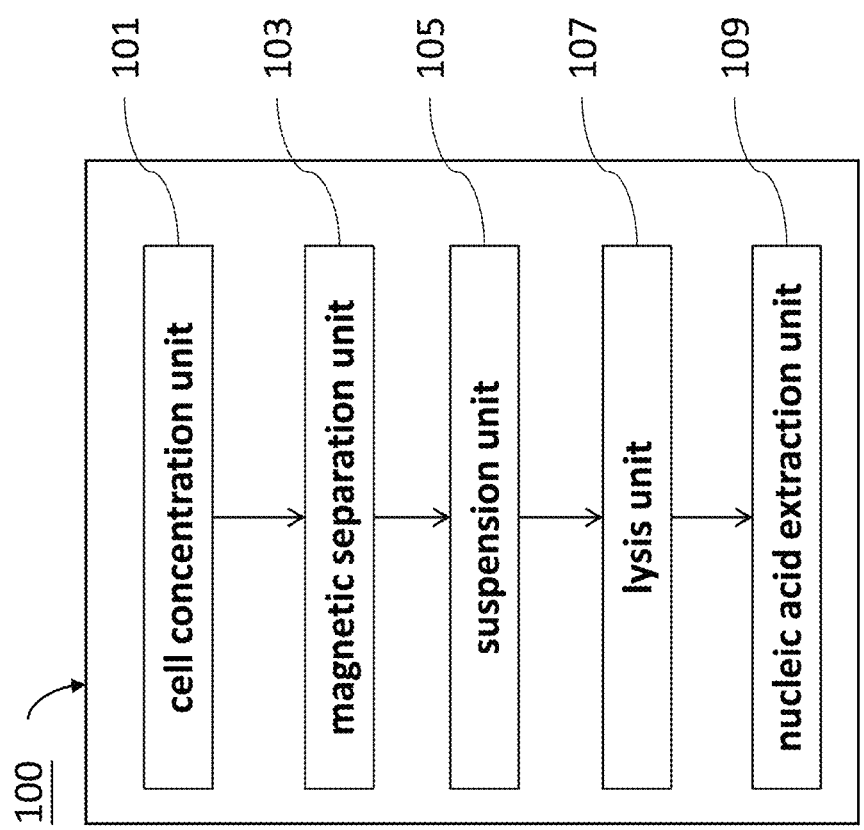
FIG. 2 shows a block diagram of the nucleic acid separation system according to an embodiment of the present invention.

The present invention further provides a system for isolating nucleic acids 100 according to the above method, as shown in FIG. 2. The system includes the following components: cell concentration unit 101, magnetic separation unit 103, suspension unit 105, lysis unit 107 and nucleic acid extraction unit 109. The operation mode and functions executed are described below. The cell concentration unit 101 is used for performing the above-mentioned cell concentration procedure, wherein the cell grabbing reagent and the magnetic carrier are mixed with the biological sample containing cells, and then the magnetic carrier forms a magnetic mass along with the cells. The magnetic separation unit 103 is used for performing the above-mentioned first magnetic separation procedure to separate the magnetic mass. The suspension unit 105 is used for adding a suspension reagent to the magnetic mass, mixing evenly, and enabling the cells to be resuspended in the suspension reagent, so as to form the first solution. The lysis unit 107 is used for performing the lysis procedure. It adds the lysis reagent into the first solution to lyse the cells in the first solution, so as to form the second solution. The nucleic acid extraction unit 109 is used for performing the nucleic acid extraction procedure to extract nucleic acids from the second solution. In this system, cell concentration unit does not use any centrifugal unit for cell concentration procedures. As for the details and characteristics of the procedures implemented by other units, they have been described previously and will not be repeated.

In view of the above description, by means of the nucleic acid isolation method and the corresponding system provided by the present invention, single and simple cell grabbing reagent is used to directly carry out the cell concentration procedure without centrifugation. Therefore, according to the technical scheme proposed in the present invention, the whole nucleic acid isolation process does not need to use any centrifugal methods, nor does it need to use special containers, test tube cartridge or replacement of equipment. Obviously, it is applicable to the existing various automated nucleic acid separation equipment. Compared with the current technology, the cell concentration procedure of the present invention can actually replace the centrifugal steps conventionally used to concentrate cells and complete the cell concentration in a more convenient way, which is very conducive to the efficiency and quality of subsequent nucleic acid extraction.

Additionally, in response to the needs of different biological samples, a clarification procedure can be used optionally to further improve the quality of nucleic acid isolation by using the clarification reagent with simple ingredients that are free of alcohols, organic solvents or chaotropic reagent to perform the clarification procedure on lysate or homogenate.

In order to explain the specific characteristics and technical effects of the present invention, the following Examples are listed.

Example 1: Cell Grabbing Reagents are Used with Different Magnetic Carrier

*E. coli* (DH5a strain cloned with TA vector, referred to as DH5a/TA) is used as a biological sample. Different cell grabbing reagents are used for different types of magnetic beads to perform the cell concentration procedures. For instance, the present Example use methanol, ethanol, isopropyl alcohol, and acetone aqueous solution as cell grabbing reagents respectively, and the traditional centrifugal method for cell concentration is used as a control. The goal is to isolate the plasmid DNA from *E. coli*, and the recovery rate of the plasmid DNA is used as an evaluation index.

At the same time, the aforementioned controlled experimental design is also applied to different types of magnetic beads for cell concentration, to assess the overall efficacy of cell grabbing reagent with different magnetic vectors. The specific evaluation indexes are the quantification results (e.g., recovery rate) and the qualitative results (e.g., gel electrophoresis images). Examples of magnetic beads herein include: silicon dioxide (silica) beads, nitrocellulose beads, polyvinyl alcohol (PVA) beads, silica beads modified by carboxyl functional groups. The following experiments are conducted according to the type of magnetic beads, which are divided into four groups: A, B, C and D, and the respective key conditions are shown in Table 1. Regarding the concentrations of the cell grabbing reagent listed in Table 1 and the context, it refers to the final concentration after the cell grabbing reagent is added to the biological sample. Therefore, when the user implements the present invention, the suitable type and appropriate volume of the cell grabbing reagent may be chosen according to their own needs. As long as the final concentration of the cell grabbing reagent falls within the stated range of the present invention, the stated technical effects of the present invention can be achieved.

TABLE 1

The experimental condition of each experimental groups according to Example 1

| Group | Magnetic beads type | Cell grabbing reagent (Percentage concentration by volume) |
|---|---|---|
| A | Silica beads | 20% methanol aqueous solution |
| | | 20% ethanol aqueous solution |
| | | 20% isopropyl alcohol aqueous solution |
| | | 20% acetone aqueous solution |
| | | Centrifugal concentration |
| | | 40% methanol aqueous solution |
| | | 40% ethanol aqueous solution |
| | | 40% isopropyl alcohol aqueous solution |
| | | 40% acetone aqueous solution |
| | | Centrifugal concentration |
| | | 60% methanol aqueous solution |
| | | 60% ethanol aqueous solution |
| | | 60% isopropyl alcohol aqueous solution |
| | | 60% acetone aqueous solution |
| | | Centrifugal concentration |
| B | Nitrocellulose beads | 20% methanol aqueous solution |
| | | 20% ethanol aqueous solution |
| | | 20% isopropyl alcohol aqueous solution |
| | | 20% acetone aqueous solution |
| | | Centrifugal concentration |
| | | 40% methanol aqueous solution |
| | | 40% ethanol aqueous solution |
| | | 40% isopropyl alcohol aqueous solution |
| | | 40% acetone aqueous solution |
| | | Centrifugal concentration |
| | | 60% methanol aqueous solution |
| | | 60% ethanol aqueous solution |
| | | 60% isopropyl alcohol aqueous solution |
| | | 60% acetone aqueous solution |
| | | Centrifugal concentration |
| C | Polyvinyl alcohol beads | 20% methanol aqueous solution |
| | | 20% ethanol aqueous solution |
| | | 20% isopropyl alcohol aqueous solution |
| | | 20% acetone aqueous solution |
| | | Centrifugal concentration |
| | | 40% methanol aqueous solution |
| | | 40% ethanol aqueous solution |
| | | 40% isopropyl alcohol aqueous solution |
| | | 40% acetone aqueous solution |
| | | Centrifugal concentration |
| | | 60% methanol aqueous solution |
| | | 60% ethanol aqueous solution |
| | | 60% isopropyl alcohol aqueous solution |
| | | 60% acetone aqueous solution |
| | | Centrifugal concentration |
| D | Silica beads modified by carboxyl functional groups | 20% methanol aqueous solution |
| | | 20% ethanol aqueous solution |
| | | 20% isopropyl alcohol aqueous solution |
| | | 20% acetone aqueous solution |
| | | Centrifugal concentration |
| | | 40% methanol aqueous solution |
| | | 40% ethanol aqueous solution |
| | | 40% isopropyl alcohol aqueous solution |
| | | 40% acetone aqueous solution |
| | | Centrifugal concentration |
| | | 60% methanol aqueous solution |
| | | 60% ethanol aqueous solution |
| | | 60% isopropyl alcohol aqueous solution |
| | | 60% acetone aqueous solution |
| | | Centrifugal concentration |

First, the cell concentration procedures of the control group and the experimental group are performed respectively:

A. Control group: centrifuge 500 μL overnight cultured DH5a/TA bacteria solution (at 13000 rpm) for 3 minutes, reserve the precipitation for subsequent nucleic acid isolation, and then remove and discarded supernatant.

B. Experimental group: add 750 μl cell grabbing reagent (type and concentration as shown in Table 1) together with 22.5 μL beads to 500 μL overnight cultured DH5a/TA bacteria solution, gently flip (or invert) to mix for 1 minute, and then placed statically in the magnetic separation device (separator) for 1 minute, until the formation of a magnetic mass which looks like precipitation, and then remove the clear supernatant.

Next, both groups are performed with the same plasmid DNA separation procedure, as follows:

1. Add 150 μL suspension buffer to the test tube and vortex to mix immediately, and resuspend the bacterial cells into the solution, followed by magnetic separation to transfer the cell suspension to the new test tube.

2. Add 150 μL lysate buffer to the test tube and mix gently to avoid genomic DNA fragmentation.

3. Add 150 μL of neutralization buffer to the test tube, mix gently and evenly, centrifuge at room temperature (13,000 rpm) to precipitate impurities, collect the supernatant and transfer it to new test tube.

4. Add 300 μL of nucleic acid binding buffer and 22.5 μL ImaBeads (Imagen Bioscience product number IB50) to the test tube and vortex to mix for 10 minutes.

5. Place the test tube in a magnetic separator for 1 minute until the ImaBeads forms a precipitated mass, then remove the supernatant of the clarified solution.

6. Add 1 mL W1 buffer (Imagen Bioscience product number IPD100-W1) and vortex for 3 minutes.

7. Place the test tube in a magnetic separator for 1 minute until the ImaBeads forms a precipitated mass, then remove the supernatant of the clarified solution.

8. Add 1 mL wash buffer (Imagen Bioscience product number IPD100-W2) and vortex for 3 minutes.

9. Place the test tube in a magnetic separator for 1 minute until the ImaBeads forms a precipitated mass, then remove the supernatant of the clarified solution.

10. Heat the test tube for 5 minutes at 60° C. to dry ImaBeads.

11. Add 50 μL of the elution buffer and vortex to mix for 10 seconds.

12. Heat the test tube statically at 60° C. for 10 minutes, during which vortex once every 3 minutes to obtain the plasmid DNA for storage.

Figure 3:
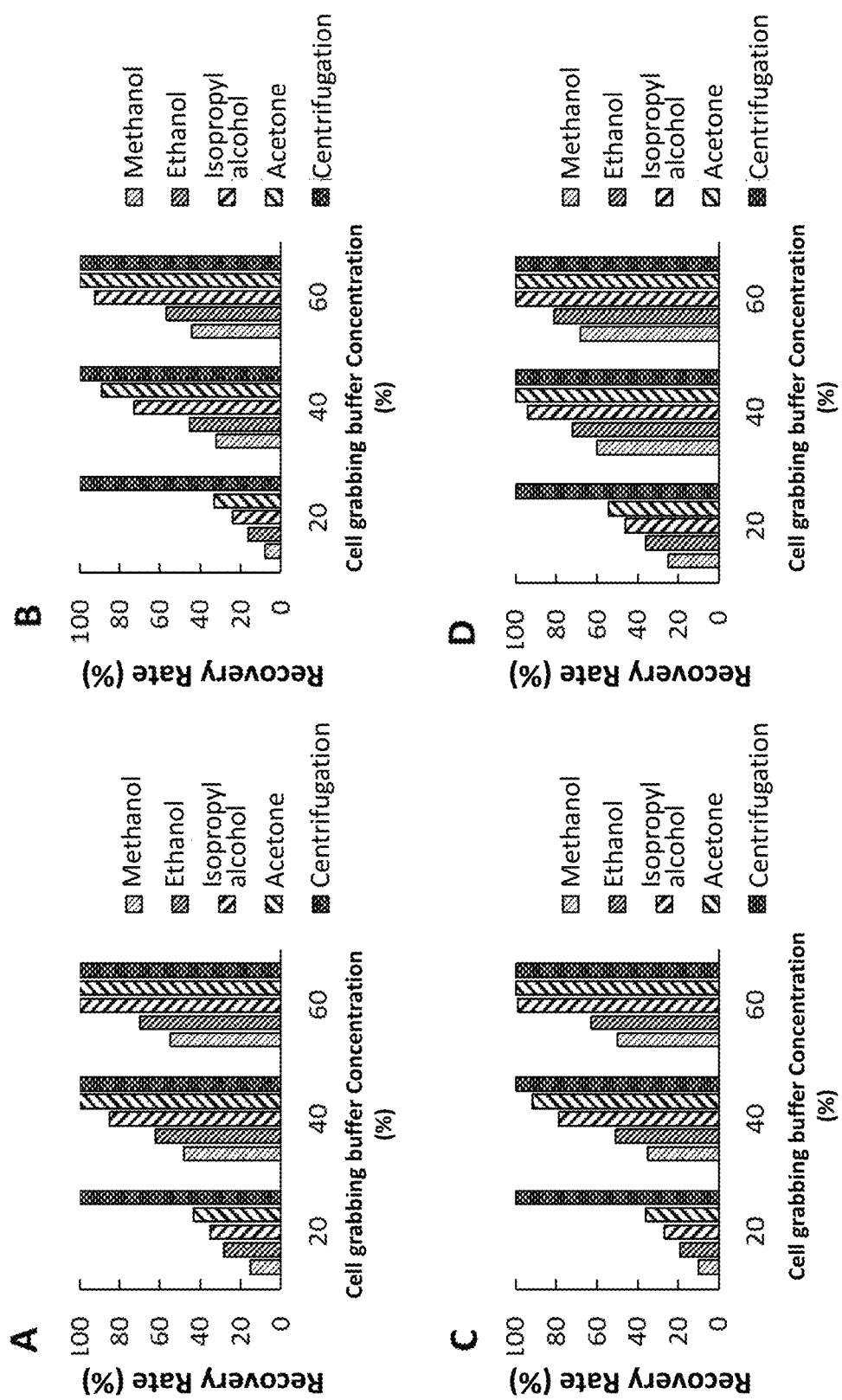
FIG. 3 shows a bar chart illustrating the results from Example 1 of the present invention.

The plasmids DNA form the abovementioned A, B, C and D groups are quantified to evaluate the recovery rate, the results are shown in FIG. 3, which shows that the four kinds of cell grabbing reagent can achieve the effect of concentrating cell by using four types of magnetic beads, and the effect of some conditions is comparable to that of conventional centrifugation methods.

Example 2: Cell Grabbing Reagents are Used with Different Biological Samples (In Vitro Cultured Cells)

First, the cell concentration procedures of the control group and the experimental group are performed respectively:

A. Control group: obtain 500 μl in vitro cultured Hela cells (containing 25% trypsin and 75% cultured medium) and centrifuge (13000 rpm) for 3 minutes, reserve the cell pellet for subsequent nucleic acid isolation, then remove and discard the supernatant.

B. Experimental group: obtain 500 μl in vitro cultured Hela cells (containing 25% trypsin and 75% cultured medium), add 500 μl cell grabbing reagents (type and concentration are shown in Table 1) and 22.5 μl ImaBeads beads, invert and mix for 1 minute, perform the magnetic separation procedure, and then remove the supernatant to proceed the nucleic acid isolation.

Next, both groups are performed with the same genomic DNA magnetic separation procedure, as follows:

1. Add 200 μL PBS and 20 μL Proteinase K (10 mg/ml) to the cell pellet and react for 10 minutes at 56° C.

2. Add 1 μL RNase A (50 mg/ml) and react at room temperature for 5 minutes.

3. Add 200 μL IGB buffer (Imagen Bioscience product number—IGB) and React for 10 minutes at 56° C.

4. Add 200 μL nucleic acid binding buffer and vortex for 10 minutes.

5. Perform magnetic separation and remove the supernatant.

6. Immediately after adding 1.0 ml W1 buffer, vortex for 3 minutes to mix adequately.

7. Perform magnetic separation and remove the supernatant.

8. Repeat the step 5 and step 6.

9 Immediately after adding 1 mL wash buffer, vortex for 3 minutes to mix adequately.

10. Perform magnetic separation and remove the supernatant.

11. Repeat the step 8 and step 9.

12. Add 100 μL of elution buffer and react for 10 minutes at 56° C., during which vortex once every 3 minutes to mix adequately.

13. Perform magnetic separation, and the supernatant (containing genomic DNA) to new test tube for storage.

Figure 4:
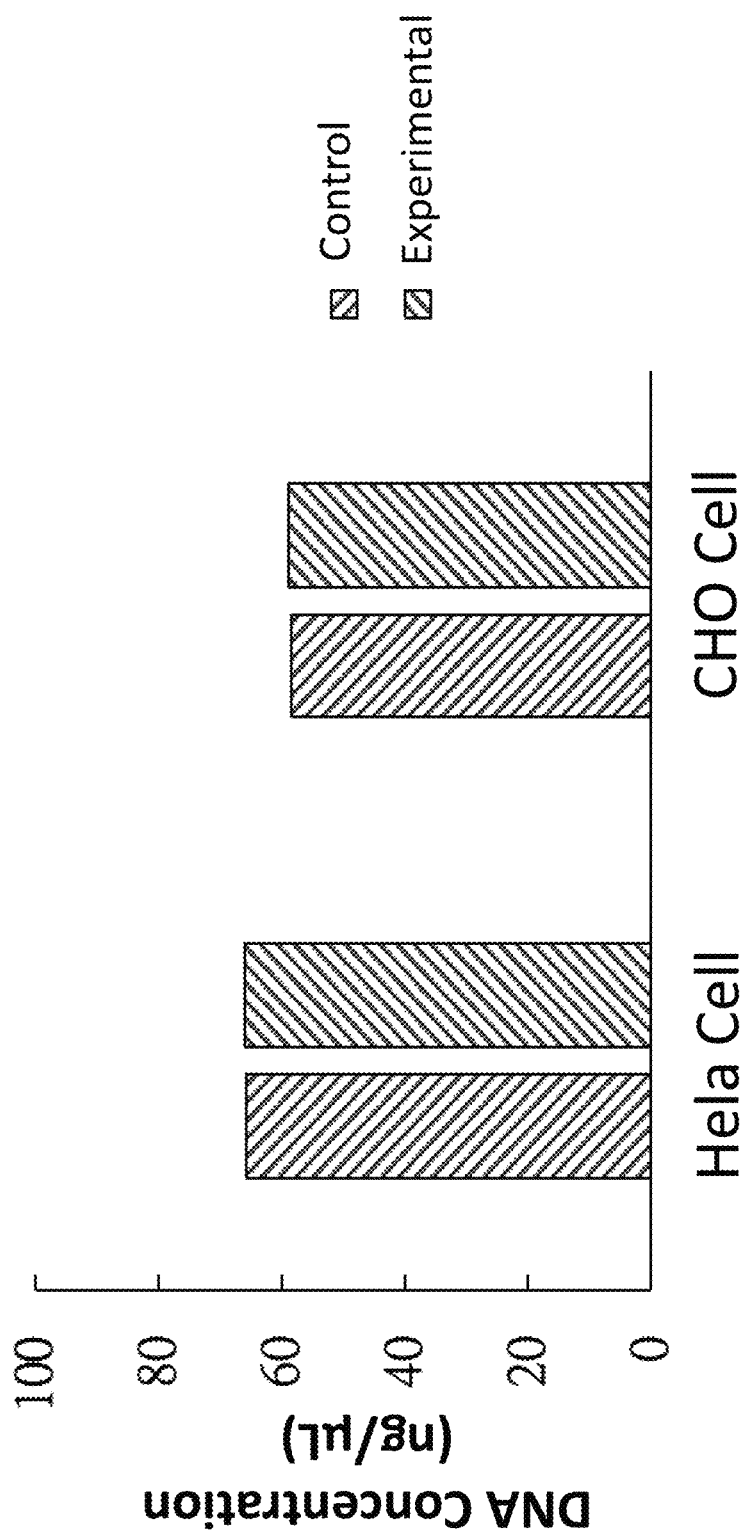
FIG. 4 shows a bar chart illustrating the results from Example 2 of the present invention.

In addition to the use of Hela cells from human sources, CHO cells from different species (from hamster) are used for performing the same experiment, and the process is not detailed herein. It should be emphasized that in this example, all steps are performed on the currently available automated magnetic separation system from the beginning of the cell concentration procedure to the nucleic acid extraction process. The isolated DNA from Hela cells and CHO cell according to the above experimental steps are quantified, and the results of DNA concentrations are shown in FIG. 4. FIG. 4 shows that the two kinds of cell are manipulated under the effect of cell grabbing reagent, and both achieve ideal nucleic acid isolation results. It fully demonstrates that the method and system provided by the present invention can indeed be easily applied to any fully automated isolation of nucleic acids, and its overall nucleic acid isolation performance and quality can be comparable with the those of conventional centrifugal method, and the effect of some conditions is even slightly better than the conventional centrifugal method.

Example 3: Cell Grabbing Reagents are Used with Different Magnetic Carrier (Whole Blood)

The overall experimental objectives of Example 3 are similar to those of Example 2, the main difference is that Example 3 uses whole blood as a biological sample. Whole blood is extensively used as a biological sample in clinical settings. Additionally, this Example further uses three different types of beads for automated process (silicon dioxide beads, nitrocellulose beads, polyvinyl alcohol beads) for the same experimental process to verify the effect of implementing the present invention.

First, the cell concentration procedures of the control group and the experimental group are performed respectively:

A. Control group: obtain 200 μl of whole blood into 2 mL microtube, add 0.6 mL RBC lysis buffer and mix it evenly by inverting the microtube; shake the mixture at 100 rpm for 5 minutes, then centrifuge (at 13000 rpm) for 1 minute, reserve the cell pellet for subsequent nucleic acid isolation, and then remove and discarded the supernatant, repeat step 2 to step 5, wash the biological sample again, and the precipitation-like cell pellet (regardless of the integrity of the cell) are used for subsequent nucleic acid isolation procedures.

B. Experimental group: obtain 200 μl of whole blood into 2 mL microtube, and after treating the whole blood with RBC lysis buffer, add 250 μl cell grabbing reagents (type and concentration are shown in Table 1) and 22.5 μL ImaBeads beads, invert to mix for 1 minute, perform the magnetic separation procedure, and then remove the supernatant to proceed the nucleic acid isolation.

Next, both groups are performed with the same genomic DNA magnetic separation procedure. Since the technology of automated extraction of whole blood nucleic acids is well known, and the process is similar to the separation procedures of Example 2, so that skilled persons in the field can readily understand how it is implemented, it is no longer repeated.

Figure 5:
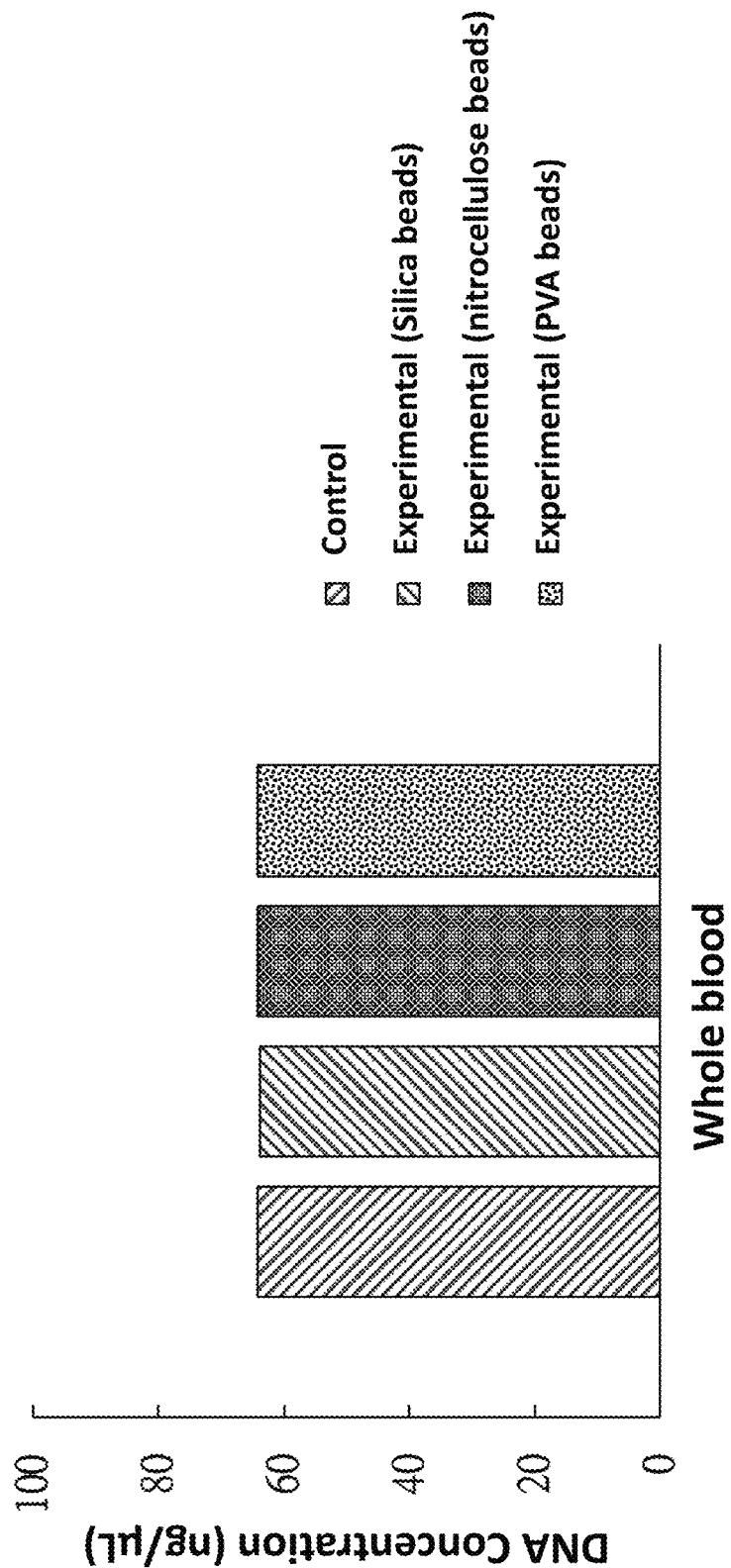
FIG. 5 shows a bar chart illustrating the results from Example 3 of the present invention.

In this Example, all steps are performed on the currently available automated magnetic separation system from the beginning of the cell concentration procedures to the nucleic acid extraction process. The isolated DNA from whole blood according to the above experimental steps are quantified, and the results of DNA concentrations are shown in FIG. 5. FIG. 5 shows that the whole blood is manipulated under the effect of cell grabbing reagent to achieve ideal nucleic acid isolation results, and it works well in all the three types of magnetic beads system. It fully demonstrates that the method and system provided by the present invention can indeed be easily applied to any fully automated isolation of nucleic acids, and its overall nucleic acid isolation performance and quality can be comparable with the those of conventional centrifugal method, and the effect of some conditions is even slightly better than the conventional centrifugal method.

Example 4: Cell Grabbing Reagents are Used with Different Biological Samples (Semen Sample)

The experimental group of the present example uses semen as biological sample. According to the method and automation system provided by the present invention, the cell concentration procedure is carried out at beginning with the cell grabbing reagent (type and concentration as shown in Table 1), and finally the genomic DNA (nucleic acid extraction procedure) is extracted using magnetic separation method. On the other hand, the control group consistently uses centrifugal methods to collect and concentrate cells, and eventually uses magnetic separation methods to extract genomic DNA (nucleic acid extraction procedures). The results of genomic DNA concentration and its absorbance obtained in accordance with this embodiment are shown in Table 3. It demonstrates that the automated nucleic acid separation method provided by the present invention has excellent effects, and the performance is even better than the conventional procedure represented by the control group.

TABLE 3

The performance of nucleic acid isolation according to Example 4.

| Group | Genomic DNA concentration (ng/µL) | Recovery rate | Absorbance 260/280 | Absorbance 260/230 |
|---|---|---|---|---|
| Control group | 84.45 | 100.00% | 1.81 | 2.07 |
| Experimental group | 82.76 | 98% | 1.83 | 2.01 |

Example 5: Clarification Procedure (Using Organic Solvent-Base Aqueous Solution as Clarification Reagent)

As mentioned earlier, to improve the quality of nucleic acid separation, one of the existing technical means is to use clarification steps or related procedures to reduce impurities. However, most of the reagents currently used for clarification are aqueous solutions containing chaotropic salts, alcohol-based aqueous solutions, or aqueous solution of other organic solvents. Although the purpose of clarifying lysate or homogenate can be achieved by these conventional approaches, there are existing problems of residual nucleic acids and incomplete recovery.

Figure 6:
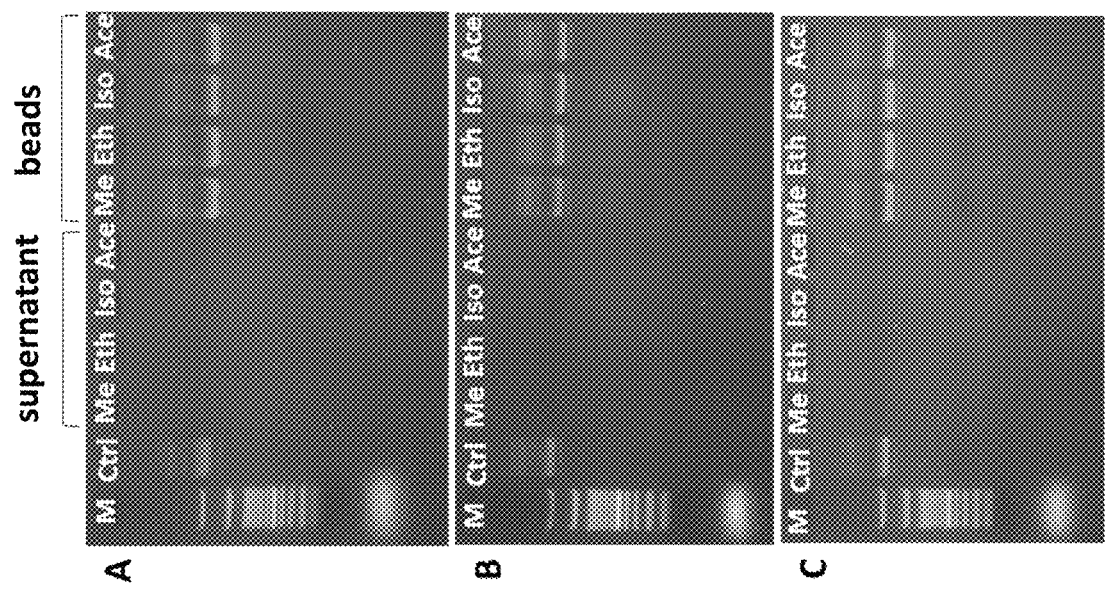
FIG. 6 shows an image of gel electrophoresis according to Example 5 of the present invention.

In view of this disadvantage, this Example takes four kinds of solvent often used to clarify procedures for instance. The provided four clarification reagents are: 60% methanol aqueous solution (Me), 60% ethanol aqueous solution (Eth), 60% isopropyl alcohol aqueous solution (Iso), and 60% acetone aqueous solution (Ace), and these clarification reagents are tested in three magnetic bead systems: silicon dioxide/silica beads (Group A), nitrocellulose beads (Group B), and polyvinyl alcohol beads (Group C) respectively. In this Example, DH5a/TA cultured solution is concentrated by traditional centrifugal methods to obtain bacterial cells, followed by lysis and nucleic acid separation (detailed execution steps are substantially similar to the aforementioned examples and are no longer described redundantly). The plasmid DNA, supernatant left after magnetic separating the beads adsorbed nucleic acids, and the left beads after elution were all analyzed by electrophoresis to assess the residual nucleic acid on the magnetic beads after nucleic acid separation, and the results are shown in FIG. 6. The results of DNA ladder or DNA marker (M, standard lane) and the plasmid DNA obtained from the extraction (Ctrl) are used as references. As shown in FIG. 6, the use of organic solvent-based clarification reagents results in nucleic acid remnants (the plasmid DNA in this case) on the beads, which inevitably affect the recovery rate.

In this regard, the present invention aims at eliminating the shortcomings of using organic solvent aqueous solution as a clarification reagent, and provides a simple and effective clarification reagent, which can not only easily replace the existing clarification reagent, but also coordinated with the aforementioned cell grabbing reagent and its methods, further improve the performance of nucleic acid isolation. The specific example will be listed in Example 6.

Example 6: Clarification Procedure (Using Clarification Reagent and Clarification Procedure According to the Present Invention)

The present Example provides a concept of using a specific monovalent ion solution as the clarification reagent, and 10 different monovalent ion solution are listed to be used as the clarification reagents. The serial numbers representing different monovalent ion solution and their concentrations are shown in Table 2. These clarification reagents are further used in the clarification procedure of DH5a/TA lysate, mouse tissue (sampled from the kidneys, heart and spleen) lysate to assess the effect of the clarification solution. Since the manipulations for the procedure of collecting cells/tissues, concentrating cells and lysis are similar to that of the aforementioned Examples, it is easy for those skilled persons in this technical field to understand and they are no longer described to avoid redundancies. This clarification procedure is carried out after lysis, and the obtained clarified product is loaded into a transparent microtube, with untreated lysate as a reference, so that the clarification effects can be compared. The results (data not shown) suggest that the various clarification reagents listed in Table 2 can effectively achieve the goal of clarifying lysate and eliminate the disadvantages of nucleic acid residues on the beads.

TABLE 2

Monovalent ions used in clarification reagents

| Monovalent ion type | Concentration for used as clarification reagents | |
|---|---|---|
| ammonium acetate (NH$_4$OAc) | 1M | 3M |
| sodium acetate (NaOAc) | 1M | 3M |
| potassium acetate (KOAc) | 1M | 3M |
| ammonium chloride (NH$_4$Cl) | 1M | 3M |
| potassium chloride (KCl) | 1M | 3M |

Example 7: Tissue Clarification Procedure (Using Clarification Reagent and Clarification Procedure According to the Present Invention)

The present invention provides a method and its system of using specific monovalent ion solutions as clarification reagents. In fact, this method and its system can replace the currently used clarification reagents, and it can be widely used with various types of magnetic beads and a variety of biological samples, including living tissues. The present example uses there kinds of mouse organ tissues (kidney, heart and spleen)(10 mg) as biological samples, and the conventional clarification procedure are used as the control. The purpose is to demonstrate the effects of the method and system on nucleic acid isolation in three types of magnetic beads systems (silica beads, nitrocellulose beads, and polyvinyl alcohol beads).

Figure 7:
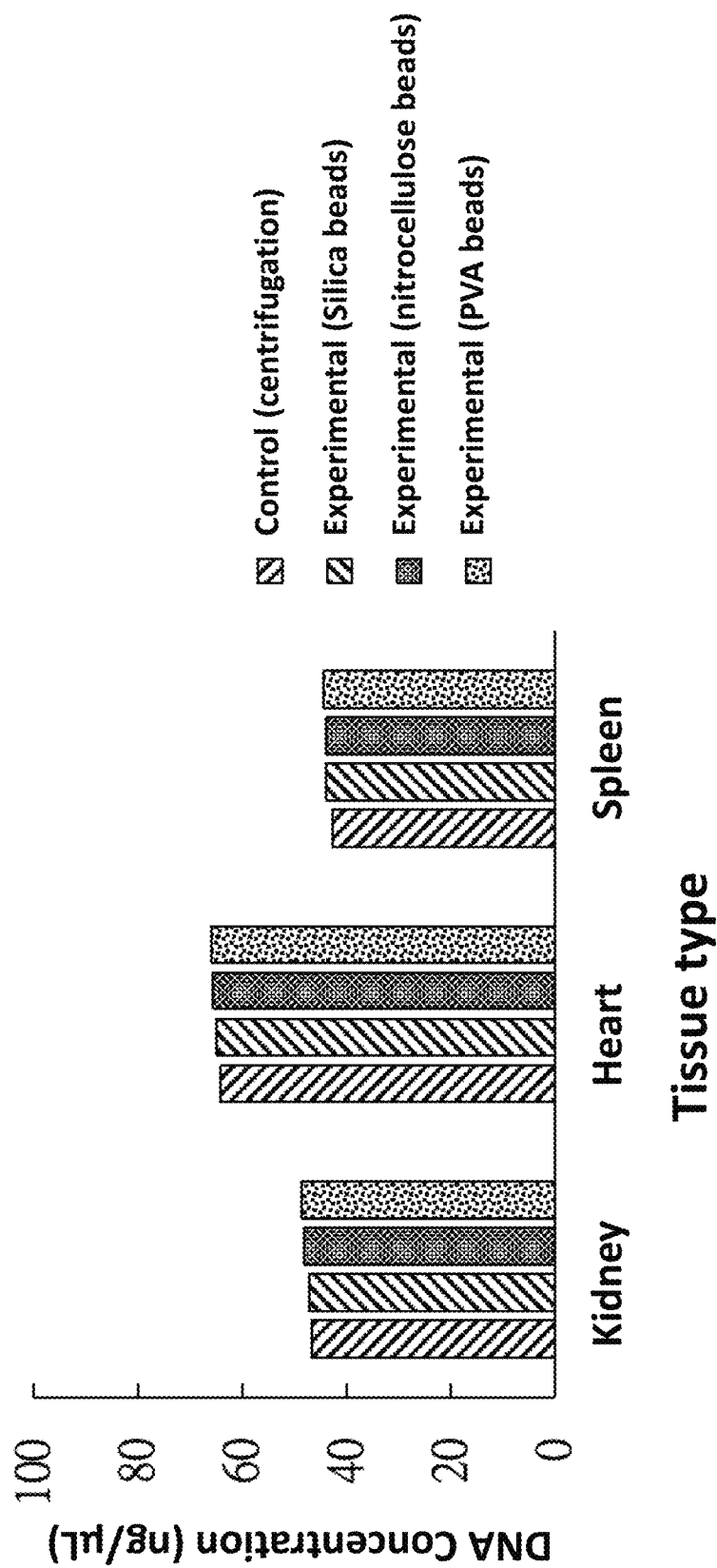
FIG. 7 shows a bar chart illustrating the results from Example 7 of the present invention.

Since the pre-processing procedures, the lysis procedure and the following magnetic separation procedure of living tissues can be easily understood by skilled persons in the field, and the difference between this Example and the conventional means lies in replacing the conventional clarification procedure with the clarification procedure implemented by using specific monovalent ion solution (type and concentration as shown in Table 2), and the remaining operating methods are generally similar or consistent with the common magnetic nucleic acid separation method, so the relevant operational details are no longer described. The experimental Example uses the DNA concentration obtained by magnetic separation as an index, and the results are shown in FIG. 7. It shows that the clarification procedure based on the clarification reagent provided by the present invention not only simplifies the operation steps and reagents but also can be applied to different tissues and different magnetic beads systems. The resultant nucleic acid isolation performance is favorable, and sometimes the performance is even better than the traditional clarification procedure.

Based on the above Examples clearly show that the present invention uses cell grabbing reagents and clarification reagents to provide the method and its system for replacing many conventional methods, and the provided method and its system achieve the comparably excellent nucleic acid isolation results. Therefore, Examples are further listed to explain the joint use of the cell concentration procedures and clarification procedures according to the present invention to demonstrate the nucleic acid isolation results. For simplicity, the following description is focused on the main parameters or observational objectives to list and interpret the results. Details of technical skills commonly used and technologies easily understood by those skilled persons in the field are no longer detailed.

Example 8: Nucleic Acid Isolation for Different Biological Samples (Cloned Bacterial Strains)

Figure 8:
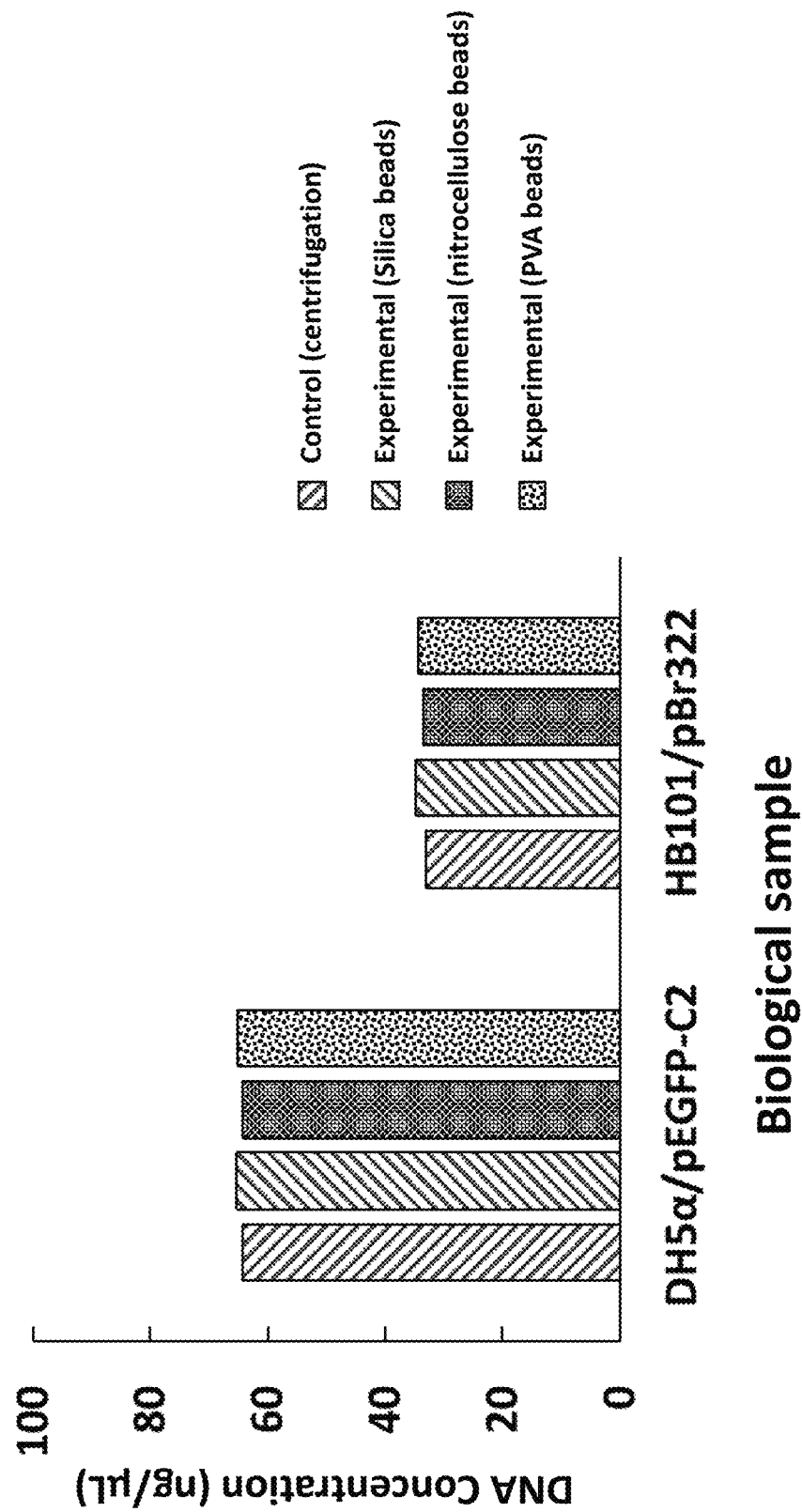
FIG. 8 shows a bar chart illustrating the results from Example 8 of the present invention.

The experimental group of this Example obtained biological samples for different *E. coli* strains: DH5a strain carrying pEGFP-C2 vector (DH5a/pEGFP-C2) and HB101 strain carrying pBr322 vector (HB101/pBr322). According to the method and automated system provided by the present invention, the cell concentration procedure is carried out first by using the cell grabbing reagent (type and concentration as shown in Table 1), then the clarification procedure is performed by using th clarification reagent (type and concentration as shown in Table 2), and at the same time neutralization is achieved, and finally the plasmid DNA is extracted by magnetic separation method. Besides, the present Example applies this process in three types of magnetic beads system: silica beads, nitrocellulose beads, and polyvinyl alcohol beads, to evaluate their application for general purpose. On the other hand, the control group consistently uses centrifugal methods to collect and concentrate cells, uses clarification procedure, and eventually uses magnetic separation methods to extract plasmid DNA. The results of this Example are shown in FIG. 8, suggesting that the favorable effects of the automated method according to the present invention. The results also imply that the effects are even superior to the conventional procedures represented by the control group.

Example 9: Nucleic Acid Isolation for Different Biological Samples (FFPE Samples)

Regarding the largely demanded FFPE samples in clinically settings, the same methods and systems provided in the present invention can be applied as well, and the present Example further illustrates the key points for using FFPE as the biological samples. For the experimental groups, first, obtain the FFPE tissue sample of different sizes, and then classify the sample as large, medium and small tissues according to the size of the tissue. For instance, based on th FFPE slide samples with a common thickness of 5 m, a general classification can be made in accordance with the area of the section plane: large tissue is approximately 200 cm$^2$, medium tissue is approximately 120 cm$^2$, and small tissue is approximately 50 cm$^2$. Deparaffinize the above three types of FFPE tissue, and then add the appropriate amount of cell grabbing reagents and mix evenly to complete the cell (especially referred to the fixed and embedded cells in FFPE) concentration procedure. Next, perform a magnetic separation procedure to obtain the magnetic mass for lysis procedure. Then add the clarification reagent to the lysate to perform the clarification procedure. Next, obtain the supernatant by magnetic separation. Finally, use the magnetic device (separator) to perform the nucleic acid extraction procedure and obtain the nucleic acids.

On the other hand, as for the control group, the three FFPE tissue samples of different size are also used. First, deparaffinize FFPE tissue samples to obtain the precipitated pellet containing cells and debris by centrifugation. Next, the lysis procedure is performed on the pellet to obtain the lysate, and then the lysate is clarified by using centrifugation as the clarification procedure, so that impurities are precipitated and the supernatant is obtained. Finally, the magnetic device is used (under the same conditions as the experimental group) to perform the nucleic acid extraction procedure for obtaining the nucleic acids.

Figure 9:
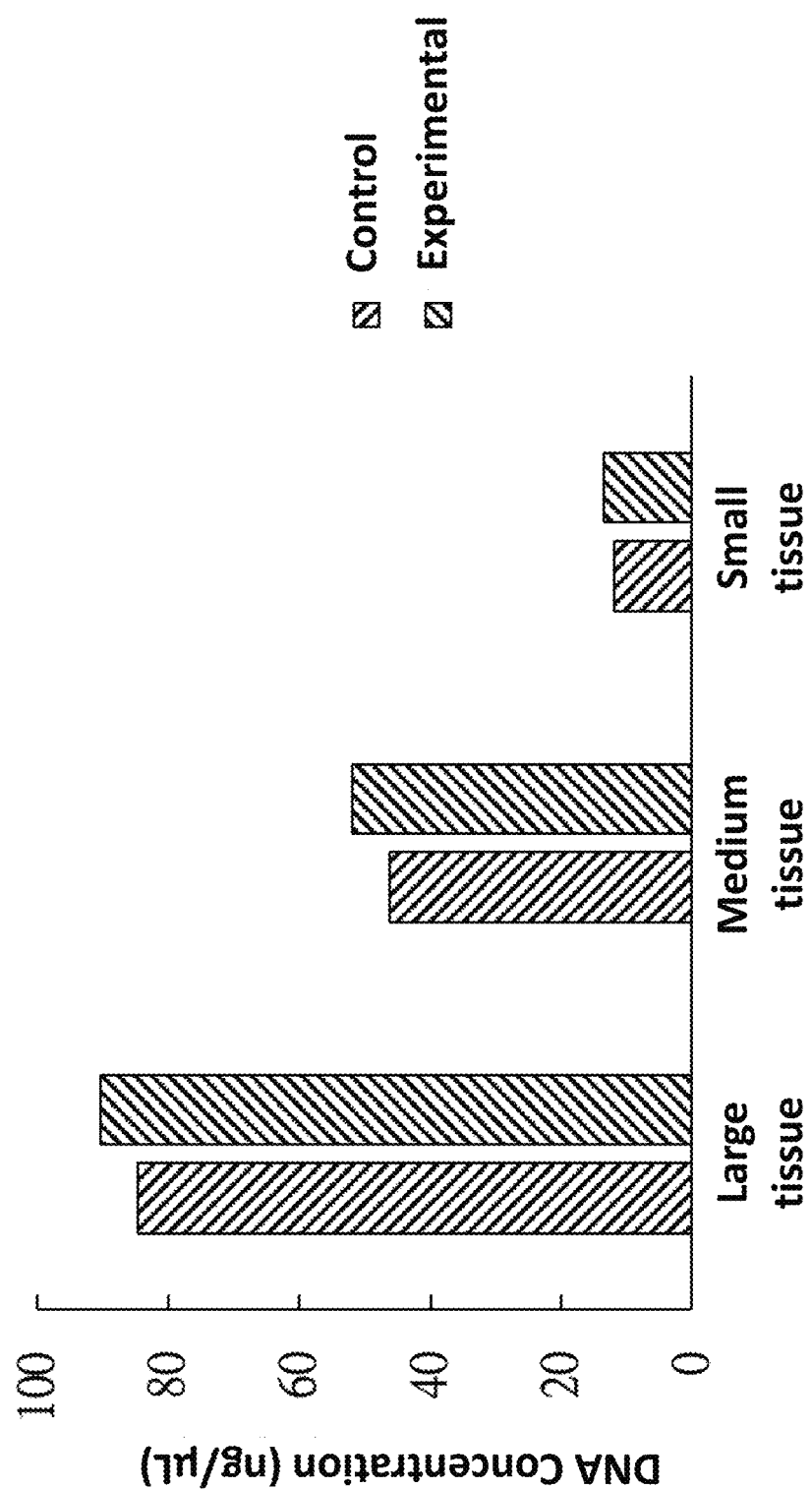
FIG. 9 shows a bar chart illustrating the results from Example 9 of the present invention.

Comparing the experimental results of the experimental group with that of the control group (FIG. 9), it suggests that regardless of the tissue size of the biological sample, the experimental group achieve an ideal results of nucleic acid isolation, showing that the nucleic acid isolation method and system provided in the present invention can meet the needs for isolating nucleic acids from FFPE samples.

In view of above Examples, it can be clearly and concretely understood that, aiming at the process of isolating nucleic acids from biological sample according to the user's needs, the present invention provides a simple and easy-to-obtain cell grabbing reagent and clarification reagent, which can be used in any combination of commercially available and commonly used reagent systems, such as various suspension reagents, lysis reagents, washing reagents, neutralization reagents, and elution reagents and can be applied to currently available manual products or semi-automated products. In addition, because these reagents are simple to use and are not subject to device and equipment restrictions, the methods and systems provided by the present invention can be easily integrated and applied to existing automated nucleic acid separation systems, greatly improving the quality and efficiency of automated nucleic acid separation and achieving the goal of fully automated nucleic acid separation.

The above description is only exemplary description of preferable embodiments of the present invention, and is not intended to limit the scope of the present invention. Meanwhile, the above description should be clear and practicable to those skilled in the art, thus various equivalent changes and alterations may be made therein without departing from the spirit of the invention and it is intended to cover herein all such changes and alterations within the true scope of the annexed claims.

The invention claimed is:

1. A method for isolating nucleic acids, comprising the following steps:
   (1) providing a biological sample containing a plurality of cells;
   (2) performing a cell concentration procedure on the biological sample, wherein a cell grabbing reagent and a magnetic carrier which contains silica, nitrocellulose or polyvinyl alcohol are mixed with the biological sample, and then the magnetic carrier forms a magnetic mass along with the plurality of cells;
   (3) performing a first magnetic separation procedure to separate the magnetic mass;
   (4) performing a suspension procedure, adding a suspension reagent to the magnetic mass, mixing evenly, and enabling the plurality of cells to be resuspended in the suspension reagent, so as to form a first solution;
   (5) performing a lysis procedure, adding a lysis reagent into the first solution to lyse the plurality of cells in the first solution, so as to form a second solution, and performing a clarification procedure after lysing the plurality of cells, wherein a clarification reagent is added to the first solution having the lysed cells and the lysis reagent, and mixed evenly to form the second solution, where the clarification reagent is monovalent ion solution free of alcohols, ketones, or chaotropic salt reagents; and
   (6) performing a nucleic acid extraction procedure to extract nucleic acids from the second solution;
   wherein the cell concentration procedure does not involve any means of centrifugation.

2. The method for isolating nucleic acids of claim 1, wherein the cell grabbing reagent is aqueous solution containing 10 to 70 percent by volume of low-molecular-weight alcohols, acetone, or a mixture thereof.

3. A system for isolating nucleic acids, comprising:
   a cell concentration unit used for performing a cell concentration procedure, wherein a cell grabbing reagent and a magnetic carrier which contains silica, nitrocellulose or polyvinyl alcohol are mixed with a biological sample containing a plurality of cells, and then the magnetic carrier forms a magnetic mass along with the plurality of cells;
   a magnetic separation unit used for performing a first magnetic separation procedure to separate the magnetic mass;
   a suspension unit used for adding a suspension reagent to the magnetic mass, mixing evenly, and enabling the plurality of cells to be resuspended in the suspension reagent, so as to form a first solution;
   a lysis unit used for performing a lysis procedure, adding a lysis reagent into the first solution to lyse the plurality of cells in the first solution, so as to form a second solution;
   a clarification unit used for performing a clarification procedure after the plurality of cells are lysed, wherein the clarification unit provides a clarification reagent, and the clarification reagent is added to the first solution having the lysed cells and the lysis reagent, and then mixed evenly to form the second solution; and
   a nucleic acid extraction unit used for performing a nucleic acid extraction procedure to extract nucleic acids from the second solution;
   wherein the cell concentration procedure dose not utilize any centrifugation unit.

4. The system for isolating nucleic acids claim 3, wherein the clarification reagent is monovalent ion solution free of alcohols, ketones, or chaotropic salt reagents.

5. The system for isolating nucleic acids of claim 3, wherein the cell grabbing reagent is aqueous solution containing 10 to 70 percent by volume of low-molecular-weight alcohols, acetone, or a mixture thereof.

* * * * *